United States Patent [19]

Meunchen et al.

[11] Patent Number: 5,014,689

[45] Date of Patent: May 14, 1991

[54] HAND BRACE

[75] Inventors: Paul K. Meunchen; Edward T. Durkin, both of Cincinnati, Ohio

[73] Assignee: The Kendall Company, Boston, Mass.

[21] Appl. No.: 482,876

[22] Filed: Feb. 21, 1990

[51] Int. Cl.$^5$ ............................................. A61F 5/10
[52] U.S. Cl. ................................... 128/77; 2/161 A; 273/54 B
[58] Field of Search ............... 128/77, 87 R; 2/161 A, 2/162; 272/67, 119; 273/54 B

[56] References Cited

U.S. PATENT DOCUMENTS

| | | |
|---|---|---|
| 2,794,638 | 6/1957 | Risher et al. . |
| 3,238,939 | 3/1966 | Stubbs . |
| 3,512,776 | 5/1970 | Thomas, Sr. . |
| 3,533,407 | 10/1970 | Smith . |
| 3,598,408 | 8/1971 | Klose . |
| 3,728,738 | 4/1973 | Andolino . |
| 3,815,908 | 6/1974 | Hashimoto . |
| 4,183,098 | 1/1980 | Knowles, Jr. . |
| 4,309,991 | 1/1982 | DeMarco . |
| 4,366,812 | 1/1983 | Nuzzo . |
| 4,533,407 | 10/1970 | Smith . |
| 4,584,993 | 4/1986 | Nelson ................... 128/77 |
| 4,698,850 | 10/1987 | Patton, Sr. et al. ............ 128/77 X |
| 4,716,892 | 1/1988 | Brunswick ............................ 128/77 |
| 4,883,073 | 11/1989 | Aziz ................................. 128/77 X |
| 4,899,763 | 2/1990 | Sebastian et al. ................. 128/77 X |

FOREIGN PATENT DOCUMENTS 3006362 8/1981 Fed. Rep. of Germany .

OTHER PUBLICATIONS

LMB Trade Literature, p. 21, Model #205.
LMB Trade Literature, p. 20, Model #215.
AliMed Inc. Trade Literature, p. 5.
AliMed Inc. Trade Literature, p. 9.
Roylan Trade Literature, p. 12.
Comp. Equipment Corporation Literature.

*Primary Examiner*—V. Millin
*Attorney, Agent, or Firm*—Wood, Herron & Evans

[57] ABSTRACT

A hand brace having dorsal and palmer hand sections integral one with the other along a distal side of the brace, those sections being connected along a proximal side of the brace only by a web defining a finger hole through which all a user's fingers extend so that the web lies between a user's thumb and forefinger. A thumb strap integral with the palmer section connects with the dorsal section when the brace is being worn and is wrapable behind the user's thumb to provide adjustable compression over the hand's thenar eminence to aid in remediation of the DeQuerveins condition Dorsal and palmar wrist sections integral with the brace's respective dorsal and palmar hand sections, are integral one with the other along the brace's distal side. A wrist strap integral with the dorsal wrist section is of a length so that the wrist strap overlies the palmar side of a user's wrist but so that it does not extend substantially onto the dorsal side of a user's wrist. Preferably the wrist strap is of a width sufficient to connect with the brace's palmar hand section, the wrist strap thereby cooperating with and overlying the palmar side of a user's wrist and a portion of the palmar side of a user's hand to aid in limiting hand extension and flexion, as well as hand ulnar and radial deviation, to control or reduce cumulative trauma to the wrist from carpal tunnel syndrome.

19 Claims, 2 Drawing Sheets

HAND BRACE

FIELD OF THE INVENTION

This invention relates to braces. More particularly, this invention relates to hand braces.

Carpal tunnel syndrome is a common and troublesome condition that interferes with the use of a person's hand. It is caused when the median nerve that runs through the wrist is subjected to excess pressure and stress. Such often occurs in the work place because of repeated operations, e.g., assembly line steps, performed by the hand. Once symptoms of pain and tingling appear in the wrist, the carpal tunnel syndrome condition frequently worsens and permanent nerve damage can occur. The hand brace of this invention adjustably limits movement of the hand relative to the wrist, i.e., it limits flexion and extension of the hand, and it limits ulnar and radial deviation of the hand. Accordingly, the hand brace of this invention is intended to control or minimize cumulative trauma to a person's wrist which may otherwise occur, and which may otherwise result in carpal tunnel syndrome, when the wrist is exposed to excess stress through repetitive and stressful uses of the hand such as can occur in the workplace.

DeQuerveins is a condition that adversely affects use of a person's thumb. The DeQuerveins condition also often arises in the workplace in, e.g., assembly line type operations, where the thumb of a person's hand is continuously and repetitively required to perform the same manual task. The hand brace of this invention also adjustably limits movement of the thumb relative to the hand, i.e., adjustably stretches over the thenar eminence of a user's hand at the base of the thumb, thereby aiding in remediation of the DeQuerveins condition.

SUMMARY OF THE INVENTION

Accordingly, it has been a primary objective of this invention to provide an improved hand brace particularly structured to aid in reducing the adverse impact of carpal tunnel syndrome and also the DeQuerveins condition, to which a user's hand might otherwise be exposed. In accord with this objective, and in preferred form, a hand brace in accord with this invention includes dorsal and palmar hand sections integral one with the other along a distal side of the brace, those sections being connected along a proximal side of the brace only by a web which defines a finger hole through which all a user's fingers extend when the brace is being worn so that the web lies between a user's thumb and forefinger. A thumb strap integral with the palmar section is of a length sufficient to connect with the dorsal section when the brace is being worn, the strap being wrapable behind the user's thumb so as to provide adjustable compression over the hand's thenar eminence in order to aid in remediation of the DeQuerveins condition to which a user's hand may be subjected. The brace also includes dorsal and palmar wrist sections integral with the brace's respective dorsal or palmar hand sections, the wrist sections being integral one with the other along the brace's distal side. A wrist strap integral with the dorsal wrist section is of a length so that when the brace is being worn the wrist strap overlies the palmar side of a user's wrist but so that it does not extend substantially onto the dorsal side of a user's wrist. Preferably the wrist strap also is of a width sufficient to connect with the brace's palmar hand section when the brace is being worn, the wrist strap thereby cooperating with and overlying the palmar side of a user's wrist and a portion of the palmar side of a user's hand when the brace is being worn to aid in limiting hand extension and flexion movement, as well as hand ulnar and radial deviation, in order to try to control or reduce cumulative trauma to the wrist from carpal tunnel syndrome when the brace is being used.

DESCRIPTION OF THE DRAWINGS

Other objectives and advantages of the invention will be more apparent from the following detailed description taken in conjunction with the drawings in which.

DETAILED DESCRIPTION OF THE INVENTION

Figure 1:
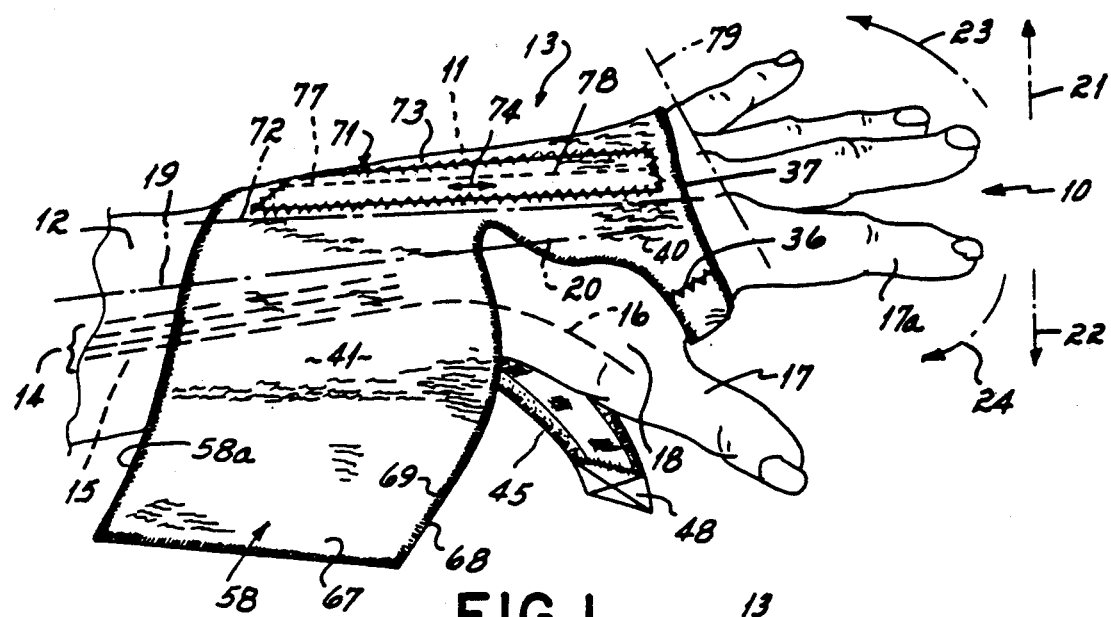
FIG. 1 is a perspective view illustrating a first step in installation of a hand brace in accord with principles of this invention on a user's hand.
Figure 2:
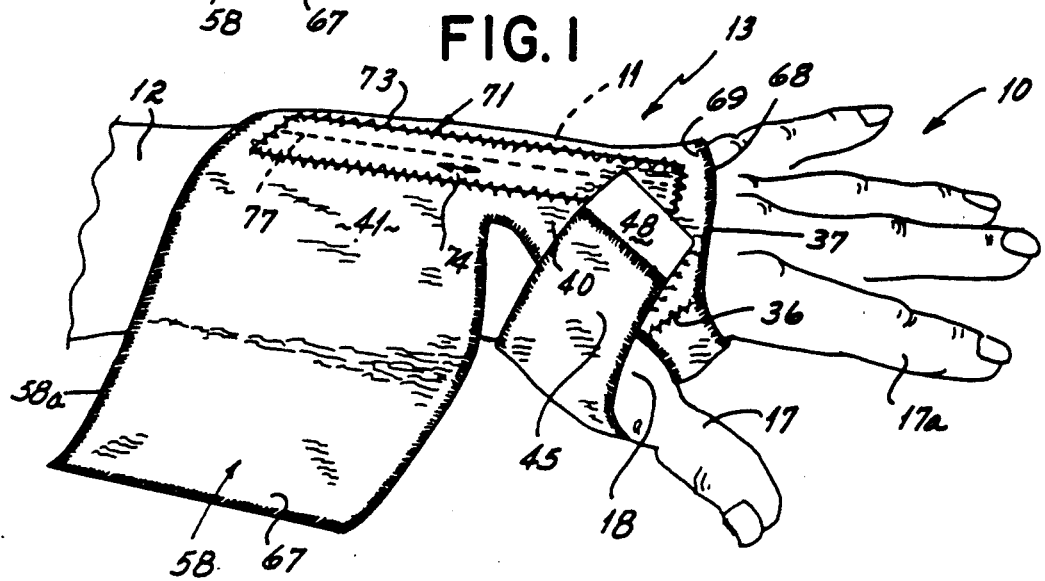
FIG. 2 is a perspective view similar to FIG. 1 illustrating a second step in installation of the hand brace.
Figure 3:
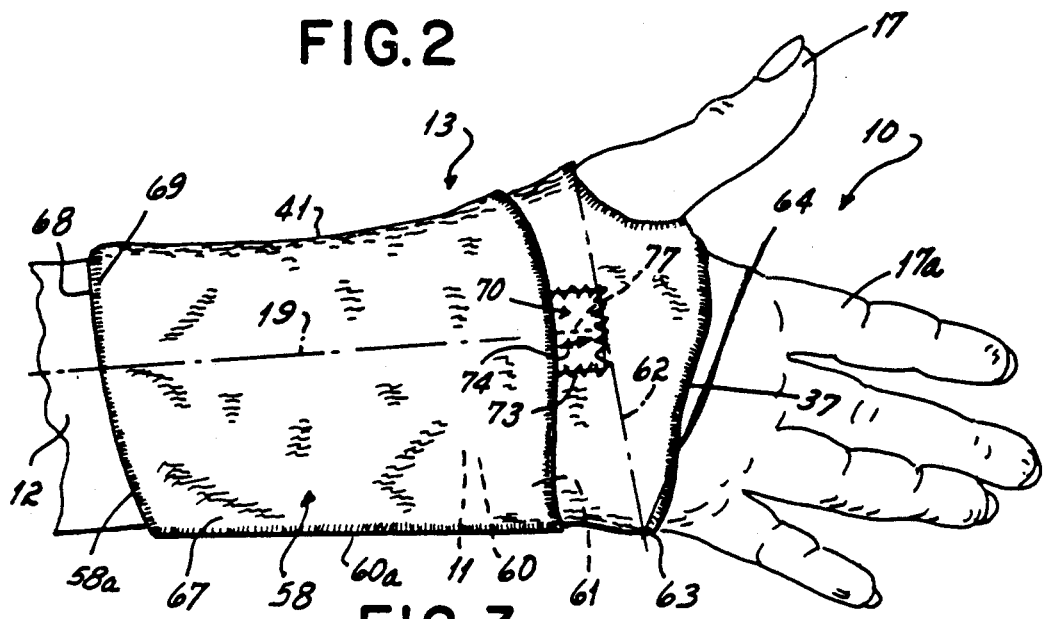
FIG. 3 is a perspective view similar to FIG. 2 illustrating a third step of installing the hand brace on a user's hand.

The hand 10, wrist 11 and arm 12 of a user on which a hand brace 13 in accord with the principles of this invention can be worn is illustrated in FIGS. 1-3. As shown in those figures, the carpal ligaments run generally beneath the wrist 11 as shown at 14, the carpal tunnel 15 passing above those carpal ligaments, i.e., is defined by those carpal ligaments. The hand 10 includes transcarpal ligaments as shown at 16 which connect with the thumb 17. These transcarpal ligaments 16 are particularly important in the thenar eminence area 18 of the thumb. Carpal tunnel syndrome is a result of injury or strain or sprain to the carpal ligaments 14 of the wrist 12. The DeQuerveins condition is due to injury or strain or sprain of the transcarpal ligaments 16 in the thenar eminence area 18 of the thumb 17. Note particularly there is illustrated a wrist axis 19, and a hand center line 20. The hand brace 13 of this invention controls flexion 21 and extension 22 of the hand and also controls ulnar 23 and radial 24 deviation of the hand, when it is adjustably and tightly installed on the hand. Further, the hand brace 13 of this invention controls movement of the thumb 17 when it is adjustably and tightly installed on the hand.

Figure 4:
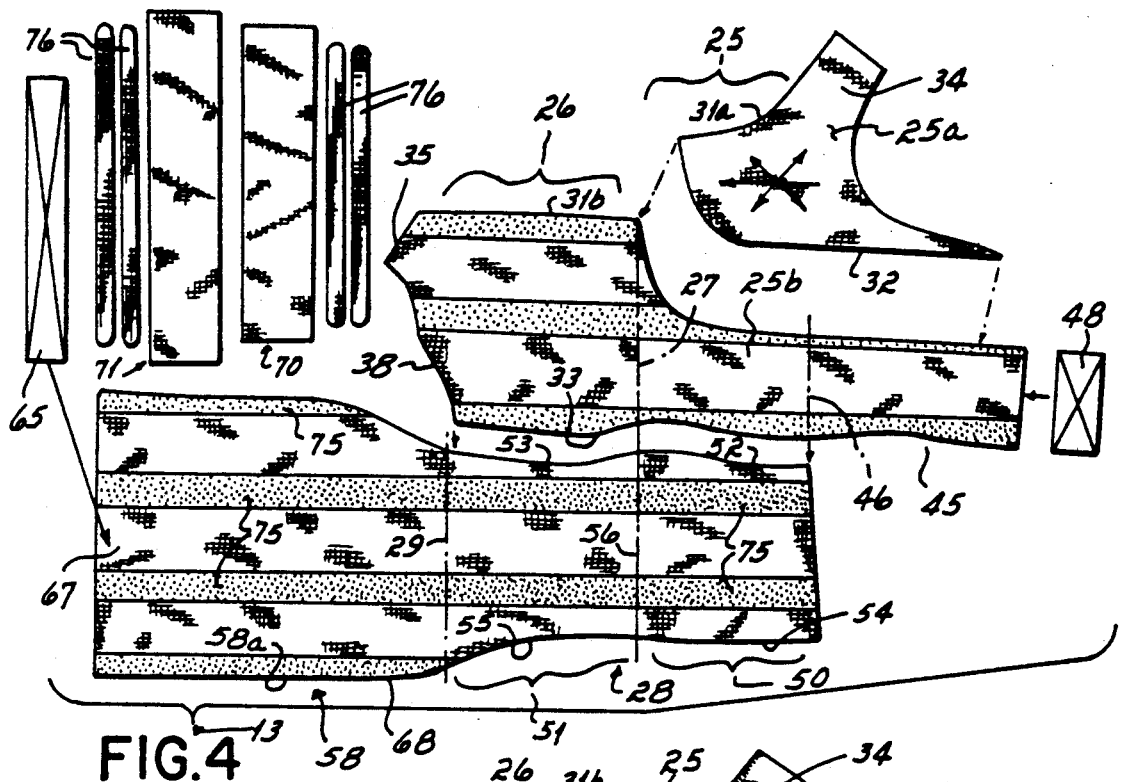
FIG. 4 is an inner side plan view illustrating the structural components of a hand brace in accord with the principles of this invention as same are cut prior to assembly.

The structural components which, when assembled together, comprise the hand brace 13 of this invention, are illustrated particularly in FIG. 4. The three major components are a palmar hand section 25, a dorsal hand section 26 (which ends at phantom line 27), and a wrist section 28 (which ends at phantom line 29). Intermediate assembly of these three sections 25, 26, 28 is illustrated in FIG. 5 where same are stitched together along stitch lines 30a, 30b.

Figure 5:
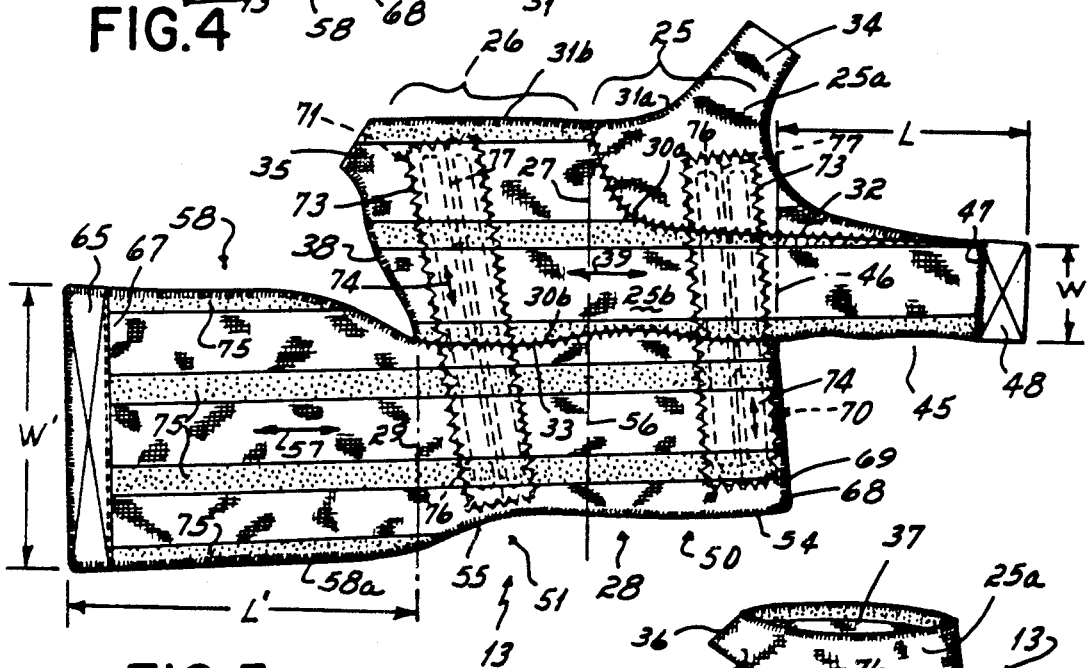
FIG. 5 is a view similar to FIG. 4 but illustrating the components stitched together in planar configuration.
Figure 6:
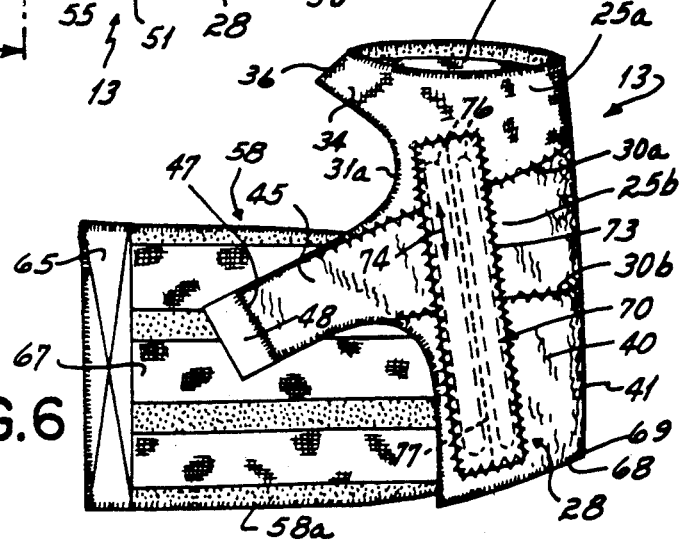
FIG. 6 is a view of the brace as assembled prior to installation on a user's hand.

The hand brace 13, shown in an intermediate assembly attitude in FIG. 5, includes the palmar hand section 25 and the dorsal hand section 26. Each of these hand sections 25, 26 defines a finger edge 31a, 31b and a wrist edge 32, 33, respectively. These palmar 25 and dorsal 26 hand sections are integral one with the other along a distal side (denoted by phantom line 27) of the brace 10 from the finger edges 31a, 31b to the wrist edges 32, 33. Each of the palmar 25 and dorsal 26 hand sections define a web area 34, 35, respectively, which are sewn together at stitch line 36 to form a hole or port 37 for the four fingers of a hand as shown in FIG. 6. Therefore, the palmar 25 and dorsal 26 hand sections are connected along a proximal side 38 of the brace 13 only by the webs 34, 35 adjacent those sections' finger edges 31a, 31b. This web 34, 35 lies between the user's thumb 17 and forefinger 17a when the brace 10 is being worn as shown in FIGS. 1-3.

The palmar hand section 25 component 25a, as illustrated in FIGS. 4 and 5, is fabricated from a material that is stretchable in all directions. Preferably, this material is a perforated neoprene with nylon fabric on both sides with a stretch or elongation at 100% of about 7 psi. This material preferably is a breathable material, and a preferred material is obtained from Rubatex, Bedford, Va. 24523. Now the dorsal hand section 26 component preferably is fabricated from an elastic fabric stretchable only in a direction 39 generally normal to the axis 19 of the user's arm 12 when the brace 13 is being worn. In this regard, preferably the material of the dorsal hand section 26 has a stretchability of about 80%. Also, and importantly, the material from which the dorsal hand section 26 is fabricated preferably is woven so as to provide a sufficient nap or pile 40 on its outer surface 41 that same acts as a loop component of a hook and loop type fastener, i.e., a loop 40 component of a Velcro hook type fastener. Preferably, this dorsal hand section 26 material is fabricated from an elastic fabric with one-way stretch which utilizes a latex gum rubber for its elastic capabilities, and a preferred source for this material is Medical Fabrics Co., Inc., Telford, Pa. 18969.

A thumb strap 45 is provided integral with the palmar hand section component 25b as shown in FIGS. 4 and 5. The thumb strap 45 extends away from the proximal side edge (defined by phantom line 46) of the palmar hand section 25b, and is of a length L sufficient to connect with the dorsal hand section 26 when the brace is being worn. The thumb strap 45, being formed of the same fabric as the dorsal hand section 26 and the palmar component 25b, is unidirectionally stretchable, and is adapted to cooperate with the dorsal hand section 26 to draw the palmer hand section 25 and dorsal hand section into an adjustably compressive brace relationship one with the other about the thenar eminence 18 area of the user's hand at the base of the thumb 17. Thus, thumb strap 45 is fabricated of a material unidirectionally stretchable primarily in a direction 39 generally normal to the axis 20 of the user's hand when the brace 10 is being worn.

As noted, a hook 48 and loop 40 type fastener is used to connect the thumb strap 45 with the dorsal hand section 26. The hook 48 section of the hook and loop 40 fastener is stitched along stitch line 47 to the end of the thumb strap 45 along the entire width W of that thumb strap. This hook section 48 of the fastener 48, 40 is adjustably connectable to the dorsal hand section 26 after that strap has been wrapped about the thumb area 18 of the user's hand as shown in FIG. 2 at whatever location on that dorsal hand section that is desired by the user. This because the pile 40 of the stretchable fabric from which the dorsal hand section 26 is formed constitutes the loop 40 portion of the fastener 48, 40.

The brace 10 also includes a palmar wrist section 50 and a dorsal wrist section 51 integral one with another as defined by the wrist section piece 28. The palmar 50 wrist section and the dorsal wrist section 51 each have a wrist edge 52, 53 and an elbow edge 54, 55, respectively, which are respectively co-extensive one with the other. The wrist edges 52, 53 of the palmar 50 and dorsal 51 wrist sections are integral with, i.e., are stitched to along stitch line 30b, the adjacent wrist edges 33 of the respective palmar 25b and dorsal 26 hand sections. The palmar 50 and dorsal 51 wrist sections are also integral one with the other along a distal side 56 of the brace from the wrist edges 52, 53 to the elbow edges 54, 55. The wrist sections 50, 51 are connected along a proximal side 29 of the brace 10 only when the brace is being worn.

The palmar 50 and dorsal 51 wrist sections are also fabricated from a fabric material that is unidirectionally stretchable only in a direction 57 generally normal to the axis 19 of the user's arm 11 when the brace 13 is being worn. The palmar 50 and dorsal 51 wrist sections are each fabricated from the same fabric as the dorsal hand section 26.

A wrist strap 58 is formed integral with the dorsal wrist section 51. This wrist strap 58 extends away from proximal side edge (denoted by phantom arrow 29) of the dorsal wrist section 51 and is of a length L' sufficient to connect with the palmar wrist section 50 when the brace 13 is being worn. The wrist strap 58 also is of a width W' sufficient to connect with the palmar hand section 25b when the brace 10 is being worn. In other words, the wrist strap 58 is of a length L' such that it overlies the palmar side 60 of a user's wrist 11 but so that it does not extend substantially beyond the distal side 60a of a user's wrist when the brace 13 is being worn. Also, the wrist strap 58 is of a width W' so that it overlies the palmar side of a user's hand in that area 61 of the hand between the wrist 11 and a phantom line 62 drawn between the base of a user's thumb and the distal end 63 of the palmar crease 64. The wrist strap 58 thereby cooperates with and overlies a portion of the palmar side of the user's hand as well as the user's wrist, when the brace 10 is being worn so as to aid in limiting hand extension 21 and flexion 22 when the brace is being worn.

The wrist strap 58 is connected with the palmar wrist section 50 and the palmar hand section 25b by a hook 65 and loop 40 type fastener. Preferably the fabric material from which the wrist section 28 is fabricated is of a loop 40 type pile. The hook 65 fastener strip is of a length equal to the width W' of the wrist strap 58 is attached to the end 67 of that wrist strap, thereby making the wrist strap attachable to the outer side 41 of the brace along the strap's entire width W'. Because the hook strip 65 can be attached to the pile 40 of the wrist 28 or hand 26 sections at any location, the wrist strap 58 is adjustably connectable to vary the tightness with which the wrist strap and the palmar hand 25b and wrist 50 sections are joined.

The exposed outer edge 68 of the hand brace 13 of this invention, i.e., the edges of the elastic fabric components 25, 26, 28, are merrowed as at 69 with a surge stitch or whip stitch. This finishing technique allows the brace 13 to have a soft stretchable finish around its outer circumference, and this finishing technique allows the product to provide substantially equal compression throughout the brace when it is installed on a user's hand. A pattern of rubberized strips 75, as shown particularly in FIGS. 5 and 6, is provided on the inner surface of at least the wrist section 28. This rubberized pattern 75 functions to aid in maintaining the brace 10 in place as desired on a user's hand. The rubberized pattern as shown is a liner pattern comprised of rubberized strips 75, and constitutes between about one third and about one half of the surface area of the wrist section 28.

A longitudinal pocket 70 is established on the outside surface 41 of the palmar side of the brace 13, and a longitudinal pocket 71 is also established on the outside surface 41 of the dorsal side of the brace. The dorsal pocket 71 is aligned generally co-axially with a line 72 between a user's wrist and a first or second knuckle on a user's hand when the brace is being worn. The palmar pocket 70 is aligned generally co-axially with the axis 19 of a user's arm when the brace 10 is being worn. Each of these pockets 70, 71 is fabricated from a fabric material identical to that from which the dorsal hand section 26, and the dorsal 51 and palmar 50 wrist sections, have been fabricated. In other words, each of these pockets 70, 71 is fabricated from a material stretchable only in one direction. And that material is sewn, as at 73 to the dorsal hand 26 and wrist 51 sections, and to the palmar hand 25, 25b and wrist 50 sections, and is placed on those sections, in such a fashion that the stretchability of that material is in a direction 74 generally parallel to the longitudinal axis of the respective pocket 70, 71. This direction 74 is also generally normal to the direction 39, 57 in which the hand 25, 26 and wrist 28 sections are stretchable.

Two spiral or quailed stays 76 are positioned within each of the dorsal 71 and palmar 70 pockets. These stays 76, which are of a type well known to the art, are flexible in flexion 21 and extension 21 directions, and also in ulnar 23 and radial 24 directions, to a limited extent when the brace 13 is being worn. These flexible stays 76 are separated one from the other within each pocket by a stitch line 77 running therebetween. When the brace 13 is being worn, the stays in dorsal pocket 71 extend from an outer end located between the center 78 of the dorsal side of a user's hand and the knuckle line 79 of a user's hand to an inner end located between a user's wrist 11 and elbow. Also when being worn, the stays in palmar pocket 70 extend from an outer end located in an area that overlies the palmar side of a user's hand to an inner end located between the user's wrist and elbow.

In use, and with a hand brace 13 fabricated as shown in FIG. 6, that brace is initially installed on a user's hand as shown in FIG. 1. In this first installation step, note the web 34, 35 area of the brace 10 is positioned between the hand's forefinger 17a and thumb 17. The web 34, 35 provides a pressure relief area, since the web's fabric material 25a is stretchable in all directions, that lends comfort to the hand.

With the brace 10 initially installed as shown in FIG. 1, the thumb strap 45 is then gripped and wrapped behind the thumb area 18 as shown in FIG. 2 with hook fastener strip 48 being secured to the pile loop fastener component defined by the fabric of the dorsal hand section 26. Because the thumb strap 45 is stretchable in the direction shown by phantom arrow 39, the compression established by the thumb strap 45 over the thenar eminence area 18 of the thumb can be adjusted by the user as desired. It is this compression on the thenar eminence area 18 of the thumb 17 which tends to alleviate discomfort brought about by the DeQuerveins condition.

The last step or third step in installing the wrist brace on a user's hand is illustrated in FIG. 3. After the thumb strap 45 has been connected with the brace's dorsal hand section 26 as shown in FIG. 2, the wrist strap 58 is then gripped by the user and wrapped around the proximal side 38 of the user's wrist and hand, compare FIG. 2 with FIG. 3. Note particularly the elbow edge 58a of the wrist strap 58 is positioned to overlie the elbow edge 54 of the palmar wrist section 50 when the wrist strap is wrapped and connected with the brace in final use configuration as shown in FIG. 3. This installed location of the wrist strap 58 ensures that the wrist strap, because of its width W', will not only cover the palmar wrist section 50 of the brace and, therefore, the user's wrist, but also will partially cover the palmar side of the user's hand, i.e., will cover a part of the heel of the user's hand. This combination connection of the wrist strap 58 with the brace's palmar wrist section 50 as well as with a portion of the brace's palmar hand section 25b enhances the stability of the brace 13 in assembly with the hand and, thereby, better controls, i.e., better limits, the flexion, extension, ulnar deviation and radial deviation of the hand. Note particularly as shown in FIG. 3 that the remote edge 67 of the wrist strap 58 connects to the distal side 60a of the wrist and hand so that it does not extend substantially onto the dorsal side of the user's wrist or the dorsal side of the user's hand when the brace is installed.

Having described in detail the preferred embodiment of our invention, what we desire to claim and protect by letters patent is:

1. A hand brace comprising a dorsal hand section and a palmar hand section, each hand section having a finger edge and a wrist edge, said hand sections being integral one with the other along a distal side of said brace from said finger edges to said wrist edges, said hand sections being connected along a proximal side of said brace by a web adjacent said finger edge, said web and said hand sections thereby defining a finger hole through which a user's fingers extend when said brace is being worn, said web lying between a user's thumb and forefinger when said brace is being worn, a thumb strap integral with one of said dorsal and palmar hand sections, said thumb strap extending away from a proximal side edge portion of that hand section to which it is connected and being of a length sufficient to connect with the other of said dorsal and palmar hand section when said brace is being worn, said thumb strap thereby being adapted to draw said dorsal and palmar hand sections into a brace relationship one with the other about the thumb area of a user's hand, a first fastener partially carried by said thumb strap and partially carried by said dorsal hand section for releasably connecting said thumb strap to said dorsal hand section, said first fastener being adjustably connectable to vary the tightness with which said dorsal and palmar hand sections are joined, a dorsal wrist section and a palmar wrist section, each wrist section having a wrist edge and an elbow edge, said wrist edges of said wrist sections being integral with the adjacent wrist edges of said respective hand sections, said wrist sections being integral one with the other along one of a distal side and a proximal side of said brace from said wrist edges to said elbow edges, said wrist sections being connected along the other of said distal and proximal sides of said brace only when said brace is being worn, a wrist strap integral with one of said dorsal and palmar wrist sections, said wrist strap extending away from a side edge portion of one of said wrist sections and being of a length sufficient to connect with the other of said wrist sections when said brace is being worn, said wrist strap being of a length such that it overlies the palmar side of a user's wrist but so that it does not extend substantially onto the dorsal side of a user's wrist when said brace is being worn, and a second fastener partially carried by said wrist strap and partially carried by said palmar wrist section for releasably connecting said wrist strap to said palmar wrist section, said second fastener being adjustably connectable to vary the tightness with which said wrist strap and said palmar wrist section are joined.

2. A brace as set forth in claim 1, said wrist sections being integral one with the other along a distal side of said brace, said wrist sections being connected along a proximal side of said brace only when said brace is being worn.

3. A brace as set forth in claim 1, said wrist strap also being of a width and a length sufficient to connect with said palmar hand section when said brace is being worn, said wrist strap thereby cooperating with and overlying portions of the palmar side of a user's wrist and hand when said brace is being worn to aid in limiting hand extension and flexion when said brace is being worn.

4. A brace as set forth in claim 3, said wrist strap overlying the palmar side of a user's hand in that area of the hand between the wrist and a phantom line drawn between the base of a user's thumb and the distal end of the palmar crease.

5. A brace as set forth in claim 1, said dorsal hand section's finger edge being proximate to a user's knuckles when said brace is being worn, and said palmar section's finger edge being proximate to a user's palmar crease when said brace is being worn.

6. A brace as set forth in claim 1, a portion of said palmar hand section being stretchable in all directions, and said dorsal hand section being stretchable only in a direction generally normal to the axis of a user's wrist when said brace is being worn.

7. A brace as set forth in claim 1, said dorsal and palmar wrist sections each being stretchable only in a direction generally normal to the axis of a user's wrist when said brace is being worn, said dorsal and palmar wrist sections being fabricated from the same material as said dorsal hand section.

8. A brace as set forth in claim 1, said thumb strap being integral with said palmar hand section, said thumb strap thereby being adapted to cooperate with said dorsal hand section to draw said palmar hand section and said dorsal hand section into a brace relationship one with the other.

9. A brace as set forth in claim 8, said thumb strap being fabricated of a material stretchable primarily in a direction normal to the axis of a user's arm when said brace is being worn.

10. A brace as set forth in claim 1, said first fastener comprising one of a hook fastener element and a loop fastener element on one of said thumb strap and said dorsal hand section and the other of said hook and loop fastener elements on the other of said thumb strap and said dorsal hand section.

11. A brace as set forth in claim 10, said fastener element on said dorsal hand section being defined by pile of the material from which said dorsal hand section is formed.

12. A brace as set forth in claim 1, said second fastener comprising one of a hook fastener element and a loop fastener element on one of said wrist strap and said palmar wrist section, and the other of said hook and loop fastener elements on the other of said wrist strap and said palmar wrist section, said fastener element on said palmar wrist section being defined by the pile of the material from which said palmar hand and wrist sections are formed.

13. A brace as set forth in claim 1, said brace comprising at least one longitudinal pocket on one of the dorsal side of said brace and the palmar side of said brace, and a spiral stay positioned within said pocket.

14. A brace as set forth in claim 13, said brace comprising at least one longitudinal pocket on the dorsal side of said brace, and at least one longitudinal pocket on the palmar side of said brace, and a spiral stay positioned within each of said dorsal and palmar pockets, said dorsal stay extending from an outer end located between the center of the dorsal side of a use's hand and the knuckle line of a user's hand to an inner end located between a user's wrist and elbow, and said palmar stay extending from an outer end located in an area that overlies the palmar side of a user's hand to an inner end located between said user's wrist and elbow, said spiral strap cooperating to limit extension, flexion, radial deviation and ulnar deviation of the hand when said brace is being worn.

15. A brace as set forth in claim 14, said dorsal pocket being aligned generally co-axially with a line between a user's wrist and a second or third knuckle on a user's hand when said brace is being worn, and said palmar pocket being aligned generally co-axially with the axis of a user's wrist when said brace is being worn, said pockets each being stretchable only in a direction generally parallel to the longitudinal axis of said pocket.

16. A brace as set forth in claim 1,
said palmar hand section being initially separate from said dorsal hand section and from said wrist sections, said dorsal hand section being initially separate also from said wrist sections, said wrist sections being initially integral one with the other, all of said sections being shaped in outline configuration so that when connected together as a finished brace same tends to conform to a user's hand and wrist when said brace is being worn.

17. A brace as set forth in claim 1, said brace comprising a rubberized pattern on the inner surface of at least said wrist sections, said rubberized pattern, functioning to aid in maintaining said brace in place as desired on a user's hand.

18. A brace as set forth in claim 17, said rubberized pattern constituting between one-third and about one-half of the surface area of said wrist sections.

19. A brace comprising a dorsal hand section and a palmar hand section, each hand section having a finger edge and a wrist edge, said hand sections being integral one with the other along a distal side of said brace from said finger edges to said wrist edges, said hand sections being connected along a proximal side of said brace by a web adjacent said finger edges, said web and said hand sections thereby defining a finger hole through which a user's fingers extend when said brace is being worn, said web lying between a user's thumb and forefinger when said brace is being worn, said dorsal hand section's finger edge being proximate to a user's knuckles when said brace is being worn, and said palmar section's finger edge being proximate to a user's palmar crease when said brace is being worn, said palmar hand section being stretchable in all directions, and said dorsal hand section being stretchable only in a direction generally normal to the axis of a user's arm when said brace is being worn, a thumb strap integral with said palmar hand section, said thumb strap extending away from a proximal side edge portion of said palmar hand section and being of a length sufficient to connect with said dorsal hand section when said brace is being worn, said thumb strap being adapted to cooperate with said dorsal hand section to draw said palmar hand section and said dorsal hand section into a brace relationship one with the other about the thumb area of a user's hand, said thumb strap being fabricated of a material stretchable primarily in a direction generally normal to the axis of a user's hand when said brace is being worn, a first fastener partially carried by said thumb strap and partially carried by said dorsal hand section for releasably connecting said thumb strap to said dorsal hand section, said first fastener being adjustably connectable to vary the tightness with which said dorsal and palmar hand sections are joined about the thumb area of a user's hand, said first fastener comprising one of a hook fastener element and a loop fastener element on one of said strap and said dorsal hand section and the other of said hook and loop fastener elements on the other of said strap and said dorsal hand section said fastener element on said dorsal hand section being defined by pile of the material from which said dorsal hand section is formed, a dorsal wrist section and a palmar wrist section, each wrist section having a wrist edge and an elbow edge, said wrist edges of said wrist sections being integral with the adjacent wrist edges of said respective hand sections, said wrist sections being integral one with the other along a distal side of said brace from said wrist edges to said elbow edges, said wrist sections being connected along a proximal side of said brace only when said brace is being worn, said wrist sections each being stretchable only in a direction generally normal to the axis of a user's arm when said brace is being worn, said wrist sections each being fabricated from the same fabric as said dorsal hand section, a wrist strap integral with said dorsal wrist section, said wrist strap extending away from a proximal side edge portion of said dorsal wrist section and being of a length sufficient to connect with said palmar wrist section when said brace is being worn, said wrist strap also being of a width and a length sufficient to connect with said palmar hand section when said brace is being worn, said wrist strap being of a length such that it overlies the palmar side of a user's wrist but so that it does not extend substantially beyond the distal side of a user's wrist when the brace is being worn, said wrist strap overlying the palmar side of a user's hand in that area of the hand between the wrist and a phantom line drawn between the base of a user's thumb and the distal end of the palmar crease, said wrist strap thereby cooperating with and overlying portion of the palmar side of a user's wrist and hand when said brace is being worn to aid in limiting hand extension and flexion when said brace is being worn, a second fastener partially carried by said wrist strap and partially carried by said palmar hand and wrist sections for releasably connecting said wrist strap to said palmar hand and wrist sections, said second fastener being adjustably connectable to vary the tightness with which said wrist strap and said palmar hand and wrist sections are joined, said second fastener comprising one of a hook fastener element and a loop fastener element on one of said wrist strap and said palmar hand and wrist sections, and the other of said hook and loop fastener elements on the other of said wrist strap and said palmar hand and wrist sections, said fastener element on said palmar hand and wrist sections being defined by pile of the material from which said palmar hand and wrist sections are formed, at least one longitudinal pocket on the dorsal side of said brace, and at least one longitudinal pocket on the palmar side of said brace, said dorsal pocket being aligned generally co-axially with a line between a user's wrist and a second or third knuckle on a user's hand when said brace is being worn, and said palmar pocket being aligned generally co-axially with the axis of a user's arm when said brace is being worn, said pockets each being stretchable only in a direction generally parallel to the longitudinal axis of said pocket, and a spiral stay positioned within each of said dorsal and palmar pockets, said dorsal stay extending from an outer end located between the center of the dorsal side of a user's hand and the knuckle line of a user's hand to an inner end located between a user's wrist and elbow, and said palmar stay extending from an outer end located in an area that overlies the palmar side of a user's hand to an inner end located between said user's wrist and elbow, said spiral stays cooperating to limit extension, flexion, radial deviation and ulnar deviation of the hand when said brace is being worn.

* * * * *